Figure 1:
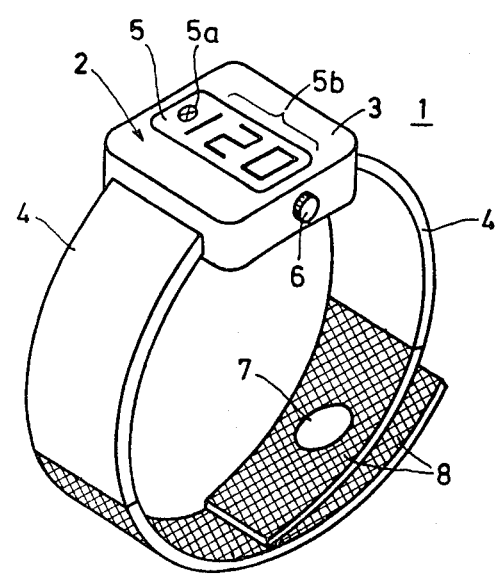

United States Patent [19]
Prinz

[11] 4,120,296
[45] Oct. 17, 1978

[54] PULSIMETER

[75] Inventor: Francois Prinz, Brügg, Switzerland

[73] Assignee: Heuer-Leonidas S.A., Berne, Switzerland

[21] Appl. No.: 693,064

[22] Filed: Jun. 3, 1976

[30] Foreign Application Priority Data
Jun. 4, 1975 [CH] Switzerland ............... 7188/75

[51] Int. Cl.² ............................................. A61B 5/02
[52] U.S. Cl. ............................................. 128/2.05 T
[58] Field of Search ............. 128/2.05 T, 2.05 P, 128/2.05 R, DIG. 15, 2.06 F

[56] References Cited
U.S. PATENT DOCUMENTS

| | | | |
|---|---|---|---|
| 3,742,937 | 7/1973 | Manuel et al. | 128/2.05 T |
| 3,807,388 | 4/1974 | Orr et al. | 128/2.05 T X |
| 3,977,393 | 8/1976 | Kovacic | 128/DIG. 15 X |
| 3,978,849 | 9/1976 | Geneen | 128/2.05 T |
| 4,022,192 | 5/1977 | Laukien | 128/2.06 F |

*Primary Examiner*—Robert W. Michell
*Assistant Examiner*—Michael H. Thaler
*Attorney, Agent, or Firm*—Pollock, VandeSande and Priddy

[57] ABSTRACT

A pulsimeter for indicating the average heart beat rate by counting the number of beats occurring during a predetermined period of time, comprising a pulse sensor adapted for flat application against a part of a human body, and an electronic counter and display preferably arranged for being worn on a person's wrist. The electronic counter and display comprise an input processing circuit which receives electrical pulses at the rate of the heart beats from the pulse sensor and which supplies to a counting circuit an electrical signal having $n$ pulses for one heart beat, $n$ being an integer factor of 60 greater than 1 and less than 60. The counting circuit repeatedly counts the pulses from the input processing circuit during the predetermined period of time, the duration of which is $60/n$ seconds. The counting circuit is reset at the end of each such period of time, just after having transmitted its end counting value to a memory circuit which supplies this value to a display during the whole next period of time. A further circuit is provided for preventing more than $n$ pulses from being delivered to the counting circuit during an interval between two consecutive heart beats. The displayed value is renewed every $60/n$ seconds, but its accuracy is the same as that which would be obtained by counting the heart beats every 60 seconds.

8 Claims, 2 Drawing Figures

PULSIMETER

This invention relates to a pulsimeter for indicating the average heart beat rate by counting the number of beats occurring during a predetermined period of time of sufficient length to offset deviations in duration liable to affect each such period taken alone.

Numerous persons suffering from cardiac afflictions must be able to monitor the average rate of their heart beat at any time in a convenient manner. It is the general aim of this invention to provide a device which enables such persons to carry out this monitoring easily, with sufficient accuracy, i.e., within a few percent, at any time and with only a slight time-lag between the beginning of a heart-beat counting period and the moment when the result of this counting is displayed.

Swiss Pat. No. 540,041 (British Patent Application No. 46151/70 filed on Sept. 29, 1970) already proposes a pulse-indicating apparatus mounted in a wrist watch which displays both the time and an indication of the heart beat rate. However, the measurement principle applied in this prior art device consists in measuring the duration of one or of a specific number of heart beat periods by counting electrical pulses recurring at a known frequency. This method is just the reverse of common medical practice, which consists in counting the number of heart beats occurring within a fixed period of time, conventionally one minute. Only in the latter case is a true indication of the average heart beat rate obtained. In the case of the aforementioned prior art apparatus, another indication of a different type is obtained, which might be called an indication of the heart beat interval duration.

Even though an indication of the duration of intervals between heart beats may be artifically converted into an indication of the average heart beat rate, the two systems of measurement are essentially different, and the system of measuring the interval duration is subject to inaccuracy owing to the instability, at very short term, of the heart beat.

German Disclosed Application No. 2,352,692 proposes a similar apparatus additionally comprising an arrangement by means of which the indication obtained by a measurement of duration is transformed into an indication of the number of beats per unit of time. The drawback of this device is the same as that mentioned in connection with Swiss Pat. No. 540,041.

Finally, in U.S. Pat. No. 3,742,937, there has also been proposed an indicator of the heart beat rate which includes a pulse sensor and a counting arrangement which counts the number of electrical pulses during a specific period, e.g., 15 seconds. This is indeed a true pulsimeter, indicating the average heart beat rate; but although it has the advantage of furnishing a value which is "renewed" every 15 seconds, it has the disadvantage of being four times less accurate, under such conditions, than an indication obtained by counting the number of beats occurring during one minute.

It is an object of this invention to provide a true pulsimeter indicating the average heart beat rate, as defined above, which, while having the advantage of a frequent renewal of the indicated value, does not present the drawback implicit in obtaining that advantage in the last-mentioned device, viz., less accuracy than apparatus counting the heart beats over a longer period of time.

To this end, the pulsimeter according to the present invention comprises a case, a counting and display portion housed within the case, and a pulse-sensing portion including a fitting suitable for gripping a part of the human body where the pulse can be detected and a sensor mounted in said fitting for application flat against the part of the human body;

the counting and display portion comprising:

an electronic circuit to which the sensor is electrically connected, a source of electrical energy mounted in the case and connected to the electronic circuit for powering the circuit, and a display device mounted within the counting and display portion;

the electronic circuit comprising:

counter means, input processing means connected to the pulse-sensing means for applying input pulses to the counter means, the number of the input pulses applied during the predetermined period of time being substantially proportionate to the number of pulse beats detected by the sensor during the period of time, the period of time being equal to $60/n$ seconds greater than 1 and less than 60, $n$ being a whole-number factor of 60, reset means for resetting the counter means at the beginning of each the period of time, memorization means for storing the value attained by the counter means at the end of each period of time and for retaining the value until the end of the following period of time, and display control means connected to the memorization means and to the display device for causing the display device to display the value contained in the memorization means, the value representing the pulse rate detected;

and the input processing means comprise:

circuit means including an input connected to receive a signal emanating from the sensor, the circuit means supplying electrical pulses reproducing the heart beats, and an output connected to the counter means and supplying a signal having substantially $n$ pulses for each pulse of the signal received at the input of the circuit means.

Figure 2:
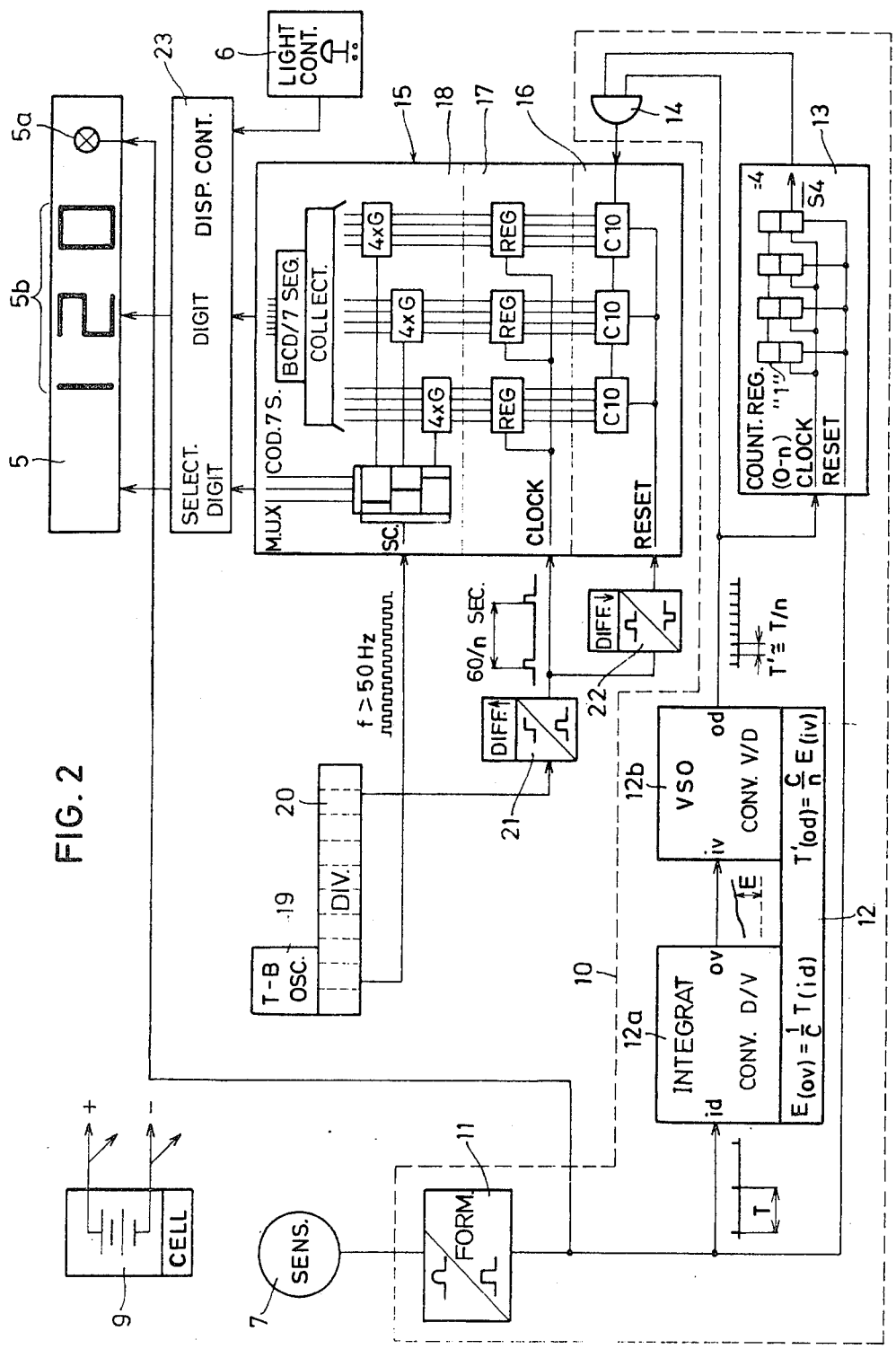

Other objects and advantages of the invention will become apparent from the following detailed description of a preferred embodiment thereof, taken in conjunction with the accompanying drawings, in which:

FIG. 1 is a perspective view of a pulsimeter according to the present invention, designed to be worn in the manner of a wrist watch, and FIG. 2 is a block diagram of the circuitry of this pulsimeter.

FIG. 1 shows a pulsimeter 1 comprising a counting and display portion 2, the components of which are accommodated in a case 3, similar to a watchcase, to which the two arms of a bracelet 4 are attached. A digital display arrangement 5 is visible on the upper face of the case 3; the display is of the seven-segment type and comprises a group 5b of three display indications for the hundreds, tens, and units, respectively. The pulsimeter 1 is designed to indicate the pulse frequency in beats per minute, so that in practice, the indication can hardly be expected to exceed the figure of 200. Hence the hundreds display indication could consist of a single segment, extinguished from 0 to 99 and lit from 100 to 199; however, in order to ensure a high degree of reliability, the pulsimeter is preferably designed to be capable, theoretically, of operating to indicate rates above 200 beats per minute; and at least for checking purposes, it is advantageous to provide a hundreds display indication suitable for displaying a numeral greater than 1 as well.

Adjacent to the digital display indications 5b, the display arrangement 5 further comprises a luminous dot 5a which flashes in rhythm with the heart beat and which not only indicates that the pulsimeter is operating and that its sensor is correctly positioned, but may also, under ordinary conditions, provide an indication which will assure the wearer that his heart is beating at an approximately normal rhythm. Whenever the wearer has the impression that the frequency is abnormally fast or slow, or if he simply wishes to know exactly what his pulse frequency is, he may press a push button 6, which will cause the luminous display 5b to appear, thus providing the digital indication of his heart beat rate.

The device operates on the basis of data obtained by means of a sensor 7 secured within one of the arms of the bracelet 4 at a point which presses against the underside of the wearer's wrist at the location where the pulse is generally taken. The bracelet 4 represents a fitting which, in a more general application, might be applied to some other part of the body where the pulse can be detected. The sensor 7 may, for example, be of a type similar to that sold by Hewlett-Packard Company, Palo Alto, California, as digital plethysmograph model 14301A. In order for the sensor 7 to operate correctly, it must be pressed firmly against the underside of the wearer's wrist, which means that the bracelet 4 must grasp the wrist securely. In order that the bracelet 4 may be fastened about the wrist in such a way as to ensure optimum positioning and tightness, the arms of the bracelet 4 are partially covered with synthetic materials 8 which adhere when pressed together, e.g., of the hooked-pile type commonly used in the clothing industry, so that the ends of the bracelet arms adhere to one another in any desired position without slipping.

FIG. 2 is a block diagram of the electronic circuitry of the pulsimeter 1 as illustrated in FIG. 1. Here the display arrangement 5, the illumination push button 6, and the heart beat sensor 7 are shown diagrammatically. A cell 9, disposed in the case 3, powers the entire circuitry of the pulsimeter 1. In the embodiment described and illustrated, provision has been made to combine most of the components into two integrated circuits 10 and 15, besides which there remain certain other components such as a time-base oscillator 19, a frequency divider 20, a positive-jump differentiation stage 21, and a negative-jump differentiation stage 22. An intermediate stage 23 for controlling the powering of the display is also shown separately but could be incorporated in the integrated circuit 15. The block enclosing the integrated circuit 15 is shown in solid lines inasmuch as it represents an integrated-circuit chip currently available on the market; the integrated circuit 10, on the other hand, merely represents a combination of various elements which have been used separately in the production of a prototype but which can be, if they have not already been, combined in a chip.

Generally speaking, the pulse signal supplied by the sensor 7 is applied to a pulse-former stage 11, the output of which supplies pulses at the rhythm of the heart beats, but at a specific amplitude and of a specific duration. The output of the stage 11 actuates the flashing display dot 5a directly. The output signal of the pulse-former stage 11 is applied to the input of a group 12 of two conjoined components 12a and 12b, the first of which is an integrator which converts the duration of the intervals between the pulses into a variable voltage E, and the second of which is a voltage-sensitive oscillator (VSO) of the relaxation type which converts the variable voltage E into an interval duration present between the pulses supplied by this oscillator, these two components being adapted to one another so that the interval between two pulses supplied at the output of the component 12b is always approximately one-quarter of the interval between two pulses received at the input of the component 12a. The interval between the heart beats is designated as T, while the interval between the pulses supplied at the output of the group 12, which is generally speaking T/n, and in this particular case T/4, is designated as T'. The logical equations and the stylized curves appearing in the drawing enable a clear understanding of the operation of the interval-reducing group 12 which, it will be appreciated, operates in effect as a frequency multiplier. It should be noted that whenever the heart beat rhythm quickens and the duration T therefore decreases, the duration T' will likewise decrease in an attempt to remain equal to one-quarter of T, but the evolution of T' will lag somewhat behind that of T. Inasmuch as the quickening of the human heart beat does not, after all, occur instantaneously, this lag in adaptation will be negligible, and the same will apply to a slowing-down of the heart beat.

The pulses leaving the group 12, separated by the interval T', are counted in a counter 16 having three decades C 10, comprised in the integrated circuit 15. The counter 16 is reset every fifteen seconds, and each time, just before it is reset, the data contained in the three decades C 10 are transmitted to a memory 17 made up of three four-bit shift registers REG also forming part of the integrated circuit 15.

For carrying out these resetting and storage operations, the device comprises a time-base oscillator 19 which supplies a frequency higher than 50 Hz, which is divided in a frequency divider 20, the last stage of which flips in one direction every fifteen seconds (generally speaking, every 60/n seconds). The accuracy of this frequency is on the order of 1%, which is sufficient in this instance. If necessary, according to the frequency of the oscillator 19, the divider 20 may also comprise feedback couplings (not shown) intended to reduce the period of 15 sec. Each time an item of output data from the divider 20 passes from the low level to the high level, a positive-jump differentiator 21, which receives these data, supplies at its output a brief pulse which is applied to the clock inputs of the registers of the memory 17, these registers then memorizing the BCD-type logic state then exhibited by the three counting decades of the counter 16. When this brief pulse ends, i.e., when the data item is already introduced into the memory 17, a negative-jump differentiator 22, the input of which receives the brief pulse in question, supplies a brief negative pulse which is applied to the reset inputs of the three counting decades C 10 of the counter 16. Moreover, since the counter 16 receives pulses at a rate four times that of the heart beats, the counter 16 will attain, during a period of 15 seconds, a state corresponding to the indication of the heart-beat rate in beats per minute (pulses four times closer, counted during a period four times shorter). Thus every fifteen seconds, the registers of the memory 17 will correct themselves in order to assume a position corresponding to the indication of the heart-beat rate calculated as a function of the number of heart beats detected by the sensor during the fifteen-second period just elapsed.

One danger which might arise if suitable precautionary measures were not taken is that a heart beat might very well fail to occur at one moment or another without the pulses supplied by the output of the voltage-sensitive oscillator 12b immediately ceasing to occur, the lack of a heart beat being at first reflected only by an increase in the interval T' between the pulses supplied by the oscillator 12b. Thus a serious cardiac deficiency would be liable to go undetected by the pulsimeter since the counter 16 would continue to receive pulses. In order to eliminate the risk, provision is made for an auxiliary counting register 13 which, by means of four flip-flops connected in series, counts the pulses supplied by the oscillator 12b starting from the moment when a heart beat is signalled by a pulse emanating from the pulse-former stage 11. The pulse supplied by the pulse-former stage 11, which pulse is likewise applied to the input of the integrator 12a and to the flashing dot 5a, resets the flip-flops of the counter 13, so that the last flip-flop of the counting register 13 will not change states until four pulses from the oscillator 12b have passed. An item of information is taken off at the inverse output S4 of this last flip-flop, this information therefore being at the logic level 1 from the moment when a heart beat is produced until the moment when four pulses have thereafter left the oscillator 12b. The output information from the counting register 13 is applied to an input of an AND-gate 14, the other input of which receives the pulses emanating from the oscillator 12b, and the output of which is connected to the counting input of the counter 16. Hence the first four pulses emanating from the oscillator 12b, starting from the moment when a heart beat is produced, will pass through the gate 14 to the counting input of the counter 16, but all pulses subsequent to the fourth one will be prevented from passing as long as a new heart beat does not intervene and reset the counter 13. Thus if a heart beat is skipped while the rhythm nevertheless remains the same, the indication of the heart beat rate will automatically be reduced by four units. Supposing, for example, that during a period of fifteen seconds, four heart beats fail to occur, the indicated value will decrease by sixteen units, which will immediately be noticed.

The integrated circuit 15 also includes a display control stage 18 comprising only a single converter BCD/7 SEG, the conversion for the three separate digital indications thus being carried out by the well-known multiplexing method. For this purpose, there is need for a scanning frequency, the period of which is less than the duration of retinal persistence. For this purpose, the frequency supplied by the oscillator 19 will be used, preferably the frequency established after passing through at least a first stage which shapes square pulses. The synchronous multiplexing information is supplied parallel to the seven-segment digit information (on seven wires) to an intermediate display control stage 23 which receives in addition information from the lighting switch 6. The stage 23 supplies energizing voltage to the segments of the display indications 5b only when the switch 6 is operated; when this is not the case, the display segments all remain extinguished, which contributes towards saving on the energy of the cell 9.

It will be noted that it would also be possible to apply the signal shaped from the sensor data directly to counter means, taking care to have these counter means advanced four steps at a time. However, four times less accuracy would then result since the sharpness of definition, i.e., the duration of the intervals counted in fifteen seconds, would be only one-quarter as good. The system described here, on the other hand, presents the advantage of achieving, by means of a measurement effected over a period of fifteen seconds, a degree of accuracy which is practically as good as that which would be achieved by means of a measurement effected over a period of sixty seconds owing to the fact that it has been possible to take into consideration the lack of any risk of an absolutely instantaneous variation of the heart beat rate (even in the case of strenuous effort, the heart takes a few dozen seconds to speed up its beat to a high rate). The technical step involved, which consists in transforming the interval T into the interval $T' = T/n$, thus proves to be extremely profitable since it enables the heart beat rate to be ascertained very quickly, viz., in fifteen seconds, while at the same time retaining the accuracy of a few percent which is normally achieved only by taking a measurement over a period of a minute.

It will be readily apparent that other embodiments might also be envisaged; for example, the counting and display portion might be accommodated in a pocket-sized case, and the sensor portion might comprise an accessory for gripping a person's wrist or finger, or even an accessory fastened to the lobe of a person's ear, in which case a fine, flexible two-wire cable would connect the counting and display portion to the sensor portion.

What is claimed is:

1. A pulsimeter for indicating the average heart beat rate by counting the number of beats occurring during a predetermined period of time of sufficient length to offset deviations in duration liable to affect each said period taken alone, comprising:

a case, a counting and display portion housed within said case, and pulse-sensing means including a fitting suitable for gripping a part of the human body where the pulse can be detected, and a sensor mounted in said fitting for application flat against said part of the human body;

said counting and display portion comprising:

an electronic circuit to which said sensor is electrically connected, a source of electrical energy mounted in said case and connected to said electronic circuit for powering said circuit, and a display device mounted within said counting and display portion;

said electronic circuit comprising:

counter means, input processing means connected to said pulse-sensing means for applying input pulses to said counter means, the number of said input pulses applied during said predetermined period of time being substantially proportionate to the number of pulse beats detected by said sensor during said period of time, said period of time being equal to $60/n$ seconds, $n$ being a whole-number factor of 60, reset means for resetting said counter means at the beginning of each said period of time, memorization means for storing the value attained by said counter means at the end of each said period of time and for retaining said value until the end of the following said period of time, and display control means connected to said memorization means and to said display device for causing said display device to display the value contained in said memorization means, said value representing the pulse rate detected;

said input processing means comprising:

pulse-former stage means receiving a signal from said sensor and supplying a pulse of fixed and predetermined duration and amplitude for each heart beat detected by said sensor, integrator stage means for converting interval duration into voltage, said integrator stage means receiving said pulses from said pulse-former stage means and supplying a voltage varying as a direct function of the duration of the intervals between said pulses from said pulse-former stage means, and voltage-sensitive oscillator stage means for converting voltage into interval duration, said voltage-sensitive oscillator stage means receiving said voltage from said integrator stage means and supplying a signal to said counter means having pulses recurring at intervals varying in duration as a direct function of said voltage, said direct functions operative in said integrator stage means and in said voltage-sensitive oscillator stage means, respectively, bearing a relationship to one another such that for any given interval T between the pulses entering said integrator stage means, said oscillator stage means supplies a signal having $n$ times as many pulses separated by an interval T' equal to T/$n$.

2. A pulsimeter in accordance with claim 1 including:

an auxiliary counter having a counting capacity at least equal to $n$, said auxiliary counter being reset each time a pulse is applied to said integrator stage means, said auxiliary counter being connected to receive for counting said pulses supplied by said voltage-sensitive oscillator stage means and being operative to supply a logic signal which changes its logic level when said auxiliary counter has counted $n$ pulses since its last resetting, and gate means having an output connected to the input of said counter means, said gate means having two inputs, one of said inputs receiving said signal supplied by said oscillator stage means and the other of said inputs receiving said logic signal from said auxiliary counter, whereby said gate means operates to allow said pulses emanating from said oscillator stage means to pass to said counter means only when, since the last resetting of said auxiliary counter, said logic signal has not yet changed its logic level, and prevents the counting of more than $n$ pulses emanating from said voltage-sensitive oscillator stage means following a heart beat in the event that the succeeding heart beat is delayed.

3. A pulsimeter in accordance with claim 1 wherein said pulse-former stage means, said integrator stage means, and said voltage-sensitive oscillator stage means comprise portions of a single integrated circuit.

4. A pulsimeter in accordance with claim 1, wherein said display device comprises digital display elements utilizing light-emitting diodes, said counting and display portion comprising switching means manually operable from the outside of said case, said switching means being connected to said display control means for causing the display of said value to appear only upon manual operation of said switching means.

5. A pulsimeter in accordance with claim 1, further comprising, for establishing said predetermined period of time equal to 60/$n$ seconds:

an autonomous oscillator operating at a frequency of at least 50 Hz and a frequency divider means including for supplying a brief control pulse every 60/$n$ seconds on the basis of the frequency of said autonomous oscillator, the beginning of said brief control pulse actuating said memorization means, and the end of said brief control pulse actuating said reset means of said counter means, said memorization means, said display control means, and said display device operating digitally, and said frequency of at least 50 Hz being used for scanning display indications of units, tens, and hundreds digits.

6. A pulsimeter in accordance with claim 1, wherein said display device comprises, in addition to means for furnishing a numerical indication of the heart beat rate, a flashing-dot display element controlled for constantly flashing in rhythm with the heart beats.

7. A pulsimeter in accordance with claim 1 intended to be worn like a wrist watch, wherein said case is a wrist-watch-type case and said fitting is a bracelet contiguous to said case, said sensor being mounted in said bracelet for application flat against the underside of a wearer's wrist.

8. A pulsimeter in accordance with claim 7, wherein said bracelet comprises two arms having ends which overlap during wearing, said ends each being provided with a covering of synthetic materials which adhere when pressed together, whereby said wrist is gripped sufficiently to ensure pressure of said sensor against said wrist underside adequate for proper operation of said pulsimeter.

* * * * *